(12) United States Patent
Marx

(10) Patent No.: US 8,399,427 B2
(45) Date of Patent: Mar. 19, 2013

(54) REAGENTS, METHODS AND SYSTEMS TO SUPPRESS PRO-INFLAMMATORY CYTOKINES

(75) Inventor: Jeffrey C. Marx, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 13/369,419

(22) Filed: Feb. 9, 2012

(65) Prior Publication Data

US 2012/0258999 A1 Oct. 11, 2012

Related U.S. Application Data

(62) Division of application No. 11/498,649, filed on Aug. 3, 2006, now Pat. No. 8,138,160.

(51) Int. Cl.
C12N 15/11 (2006.01)

(52) U.S. Cl. .................................................. 514/44 A

(58) Field of Classification Search ................. 514/44 A
See application file for complete search history.

(56) References Cited

U.S. PATENT DOCUMENTS

| | | | |
|---|---|---|---|
| 5,766,585 A | 6/1998 | Evans et al. | |
| 5,858,355 A | 1/1999 | Glorioso et al. | |
| 6,156,304 A | 12/2000 | Glorioso et al. | |
| 6,159,464 A | 12/2000 | Glorioso et al. | |
| 6,190,907 B1 | 2/2001 | Kim et al. | |
| 6,228,356 B1 | 5/2001 | Glorioso et al. | |
| 6,413,511 B1 | 7/2002 | Glorioso et al. | |
| 6,881,825 B1 | 4/2005 | Robbins et al. | |
| 7,105,494 B1 | 9/2006 | Baltzer et al. | |
| 2001/0006948 A1 | 7/2001 | Kang | |
| 2002/0048564 A1 | 4/2002 | Robbins et al. | |
| 2002/0071824 A1 | 6/2002 | Giannoukakis et al. | |
| 2002/0098168 A1 | 7/2002 | Glorioso et al. | |
| 2003/0104622 A1 | 6/2003 | Robbins et al. | |
| 2003/0140086 A1 | 7/2003 | Bollella et al. | |
| 2003/0175772 A1 | 9/2003 | Wang | |
| 2003/0219826 A1 | 11/2003 | Robbins et al. | |
| 2003/0220283 A1 | 11/2003 | Glorioso et al. | |
| 2004/0038874 A1* | 2/2004 | Omoigui .................... | 514/12 |
| 2004/0063654 A1 | 4/2004 | Davis et al. | |
| 2004/0115770 A1 | 6/2004 | Robbins et al. | |
| 2004/0161416 A1 | 8/2004 | Evans et al. | |
| 2004/0186576 A1 | 9/2004 | Biscup et al. | |
| 2004/0219145 A1 | 11/2004 | Beaman | |
| 2004/0219150 A1 | 11/2004 | Cua et al. | |
| 2004/0220130 A1 | 11/2004 | Robbins et al. | |
| 2005/0074884 A1 | 4/2005 | Robbins et al. | |
| 2005/0095246 A1 | 5/2005 | Shafer | |
| 2005/0129685 A1 | 6/2005 | Cao et al. | |
| 2005/0142114 A1 | 6/2005 | Gieseler et al. | |
| 2006/0008910 A1 | 1/2006 | Maclachlan et al. | |
| 2006/0189564 A1 | 8/2006 | Burright et al. | |
| 2006/0198825 A1* | 9/2006 | Kaemmerer et al. ........ | 424/93.2 |
| 2007/0088155 A1 | 4/2007 | Khvorova et al. | |
| 2007/0243225 A1 | 10/2007 | McKay | |
| 2007/0243228 A1 | 10/2007 | McKay | |

OTHER PUBLICATIONS

Eizema, Karin et al., Adenovirus-Based Phospholamban Antisense Expression as a Novel Approach to Improve Cardiac Contractile Dysfunction: Comparison of a Constituitive Viral Versus an Endothelin-1-Responsive Cardiac Promoter, Circulation 2000;101:2193-2199.
Wang, Jun et al., Stable and controllable RNA interference: Investigating the physiological function of glutathionylated actin, Proc Natl Acad Sci USA, Apr. 15, 2003; 100(9):5103-5106.
Iwanaga, Y. et al., Chronic phospholamban inhibition prevents progressive cardiac dysfunction and pathological remodeling alter infarction in rats, Journal of Clinical Investigation, Mar. 2004;113(5):727-736.
Del Monte, Federica et al., Targeting calcium cycling proteins in heart failure through gene transfer, Journal of Physiology 2003;546.1;49-61; originally published on line Nov. 29, 2002.
Paddison, Patrick J. et al., Stable suppression of gene expression by RNAi in mammalian cells, Proc Natl Acad Sci USA, Feb. 5, 2002;99(3):1443-1448.
Schiffelers, Raymond M. et al., Effects of Treatment With Small Interfering RNA on Joint Inflammation in Mice With Collagen-Induced Arthritis, Arthritis & Rheumatism, vol. 52, No. 4, Apr. 2005, pp. 1314-1318.
Z Hou, H.W. et al., Recovery of function in osteoarthritic chondrocytes induced by p16INK4a-specific siRNA in vitro, Rheumatology 2004;43:555-568.
Arts, Gert-Jan et al., Adenoviral Vectors Expressing siRNAs for Discovery and Validation of Gene Function, Genome Research, Sep. 15, 2003;13:2325-2332.
Tran, Nham et al., Expressing functional siRNAs in mammalian cells using convergent transcription, Bio Med Central Biotechnoly, Nov. 6, 2003;3:21.
Hosh Iji MA. M. et al., Chronic suppression of heart-failure progression by a pseudophosphorylated mutant of phospholamban via in vivo cardiac rAAV gene delivery, Nature Medicine, Aug. 2002;8(8):864-87.
Champion, H.C. et al., Robust Adenoviral and Adena-Associated Viral Gene Transfer to the In Vivo Murine Heart: Application to Study of Phospholamban Physiology, Circulation; 108:2790-2797 (2003).
Miyamoto, M.I. et al., Adenoviral gene transfer of SERCA2a improves left-ventricular function in aortic-banded rats in transition to heart failure, Proc Natl Acad Sci USA;97:293-798 (2000).
Behlke, Mark A., Progress towards in Vivo Use of siRNAs, Molecular Therapy (2006).
Kettner-Buhrow, Daniela et al., Suppression of Stable Cytokine mRNAs Using siRNA Oligonucleotides, MWG-Biotech; AN053 (2005).
Bonnet, C.S. et al., Osteoarthritis, angiogenesis and inflammation, Rheumatology;131-142 (2005).
Riley, G., The pathogenesis of tendinopathy. A molecular perspective, Rheumatology;43:131-142 (2004).
Ballara, Sundeept C. et al., New vessels, new approaches: angiogenesis as a therapeutic target in musculoskeletal disorders; Int. J. Exp. Path.;80:235-250 (1999).

* cited by examiner

*Primary Examiner* — Jon E Angell
(74) *Attorney, Agent, or Firm* — Sorell, Lenna and Schmidt LLP

(57) ABSTRACT

The present invention relates to reagents, methods and systems to treat inflammation and pain in a subject using small interfering RNA (siRNA) molecules targeted to either TNFα, IL1, IL6 and other pro-inflammatory cytokines.

15 Claims, No Drawings

SEQUENCE LISTING

```
<160> NUMBER OF SEQ ID NOS: 11

<210> SEQ ID NO 1
<211> LENGTH: 22
<212> TYPE: DNA
<213> ORGANISM: Homo sapiens

<400> SEQUENCE: 1
tttataccaa taaacggcat tt                                             22

<210> SEQ ID NO 2
<211> LENGTH: 20
<212> TYPE: DNA
<213> ORGANISM: Homo sapiens

<400> SEQUENCE: 2
ccagtgcctc tttgctgctt                                                20

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
aaatgccgtt tattggtata aa                                             22

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
aagcagcaaa gaggcactgg                                                20

<210> SEQ ID NO 5
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 5
gugccuaugu cucagccucu u                                              21

<210> SEQ ID NO 6
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
gaucaucuuc ucaaaauucu u                                              21

<210> SEQ ID NO 7
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
gacaaccaac uagguggcu u                                               21

<210> SEQ ID NO 8
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
ggagaaaguc aaccuccucu u                                              21

<210> SEQ ID NO 9
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
ggccuuccua ccuucagacu u                                              21

<210> SEQ ID NO 10
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 10
gacaaccaac uagguggugct t                                             21

<210> SEQ ID NO 11
<211> LENGTH: 21
<212> TYPE: DNA
```

```
-continued

<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 11
gugccuaugu cucagccuct t                                              21
```

REAGENTS, METHODS AND SYSTEMS TO SUPPRESS PRO-INFLAMMATORY CYTOKINES

CROSS REFERENCE TO RELATED APPLICATION

This application is a divisional of U.S. application Ser. No. 11/498,649, filed Aug. 3, 2006, the entirety of which is incorporated by reference.

FIELD OF THE INVENTION

The present invention relates to treatments for pain and inflammation using implant depots to deliver small interfering RNA (siRNA) targeted to TNF-α, IL-1, IL-6 and other pro-inflammatory cytokines into or adjacent to intervertebral discs or articulating joints.

BACKGROUND OF THE INVENTION

Pro-inflammatory cytokines are produced predominantly by activated immune cells such as microglia and are involved in the amplification of inflammatory reactions. These include IL-1, IL-6, TNF-α, and TGF-β. By way of example only, tumor necrosis factor alpha (TNF-α) appears early in the inflammatory cascade following infection or injury. It is produced by monocytes, macrophages, and T lymphocytes. TNF-α exerts its primary effects on monocytes, synovial macrophages, fibroblasts, chondrocytes, and endothelial cells, and stimulates proinflammatory cytokine and chemokine synthesis. It activates granulocytes, and increases MHC Class II expression. It promotes secretion of matrix metalloproteinases (MMPs), leading to cartilage matrix degradation. Because it initiates an inflammatory cascade, and has been found to be increased in close proximity to inflamed or injured tissue, TNF-α inhibition is a target for pain therapy. Pro-TNF-α is expressed on the plasma membrane, then cleaved in the extracellular domain. Trimerization is required for biological activity. TNF-α acts through two receptors (TNFRs): Type I receptors (p60, p55, CD 120a) are expressed constitutively on most cell types and Type II receptors (p80, p75, CD 120b) are inducible. Popular TNF-α inhibitors act primarily to inhibit binding of TNF-α to its receptors. There are currently two major classes of TNF inhibitors: 1) monoclonal antibodies to TNF-α, which prevent binding of TNF-α to its two cell-associated signaling receptors (p55 and p75) and 2) monomeric soluble forms of p55 or p75 TNFR dimerized by linking them to an immunoglobulin (Ig) Fc fragment. These Igs bind to TNF-α with high affinity and prevent it from binding to its cell-associated receptor.

TNF inhibitors have therefore been developed for therapeutic use for orthopedic and neuromuscular disease or injury that can cause pain, such as rheumatoid arthritis. TNF inhibitors currently in use are generally administered systemically via intravenous infusion and subcutaneous injection, but there are side effects of anti-TNF therapies associated with the higher doses and systemic administration that are common with these therapies. Such side effects include a limited quantity of agent that must move through the tissue to the target site in a patient, the method is inadequate to serve the needs of patients, anti-TNF therapy is generally needed over an extended period of time, so repeated injections are likely to be necessary and injection site pain and reactions sometimes develop with anti-TNF agents.

In summary, the inflammatory response is mediated by the production of catabolic cytokines by macrophages that migrate to a region of the patient attempting to remove the foreign body. The purpose of the inflammatory cascade is to promote healing of the damaged tissue, but once the tissue is healed, the inflammatory process does not necessarily end. Left unchecked, this ongoing inflammation can lead to degradation of surrounding tissues and associated chronic pain. Inflammation and its associated pain comprise a vast unmet area for patient treatment. A plethora of anti-inflammatory agents are currently on the market however and systemic administration of the more potent agents has created related health risks as noted in the withdrawal of Vioxx™ and several other drugs.

Accordingly, there is a need for novel compositions and methods of treatment for inflammation other than the systemic administration of the aforementioned compounds.

SUMMARY OF THE INVENTION

The present invention fills the foregoing need by providing reagents, methods and systems for regulating cellular levels of pro-inflamatory cytokines. Applicants have found that small interfering RNA (siRNA) molecules that correspond to at least a portion of a pro-inflammatory cytokine nucleic acid sequence are effective in inhibiting the expression of cytokines, thereby providing a means for treating inflammation and its associated pain.

Accordingly, one aspect of the present invention provides the use of implant depots to deliver a siRNA molecule to intervertebral discs or articulating joints. The siRNA molecules of the present invention correspond to at least a portion of a pro-inflammatory cytokine nucleic acid sequence capable of inhibiting expression of a pro-inflammatory cytokine in a cell. Another aspect of the present invention is directed to the use of implant depots to deliver a siRNA molecule into or adjacent to the intervertebral disc to reduce inflammation and pain. Still another aspect of the present invention is directed to the design of siRNA molecules targeting TNFα, IL1, IL6 and other pro-inflammatory cytokines coupled to a peptide transduction domain and/or inflammation with or without a biodegradable depot implant.

Another aspect of the present invention is directed to an expression vector comprising at least one DNA sequence encoding a siRNA molecule corresponding to at least a portion of a pro-inflammatory cytokine nucleic acid sequence capable of inhibiting expression of pro-inflammatory cytokine in a cell operably linked to a genetic control element capable of directing expression of said siRNA molecule in a host cell.

Another aspect of the present invention is directed to a method for inhibiting expression of pro-inflammatory cytokine in a bone cell comprising introducing into said bone cell at least one siRNA molecule that corresponds to at least a portion of a pro-inflammatory cytokine nucleic acid sequence.

Another aspect of the present invention is directed to a method for treating a subject suffering from inflammation comprising introducing into said subject at least one siRNA molecule that corresponds to at least a portion of a pro-inflammatory cytokine nucleic acid sequence.

Another aspect of the present invention is directed to a system for treating a patient suffering from inflammation comprising at least one siRNA molecule that corresponds to at least a portion of a pro-inflammatory cytokine nucleic acid sequence and a means for introducing said siRNA molecule to the desired tissue of the patient.

In a further aspect the at least one siRNA molecule that corresponds to at least a portion of a pro-inflammatory cytokine nucleic acid sequence can be introduced into the desired tissue by means of an injection, a pump or a depot.

In the practice of the invention, a siRNA depot implant is implanted in a subject at or near a target site. Non-limiting examples of such sites include an inflamed nerve, a synovial joint, or a spinal site, in particular a spinal disc site, such as the spinal disc space, the spinal canal or the surrounding soft tissue.

In another embodiment of the invention the siRNA depot implant is positioned in the knee joint, thereby eluting the siRNA, into the knee joint synovial fluid. Additional embodiments of the invention provide for positioning the drug depot implant in the shoulder, hip, other joints or spine of a patient.

In one embodiment, a targeted delivery system of one or more siRNA molecules is conveniently a catheter. In another embodiment, the targeted delivery system is a syringe.

In one method of the invention, the targeted delivery system comprises a drug depot implant system administered locally by insertion of a catheter at or near a target site, the catheter having a proximal end and a distal end, the distal end having an opening to deliver a siRNA in situ, the proximal end being fluidly connected to a pharmaceutical delivery pump. For example, the proximal end of the catheter may deliver the siRNA molecule to within 10 cm of a target site, more particularly, to within 5 cm of the target site.

In the employment of an implant of the invention, the siRNA molecule may inhibit inflammation mediated by TNF-α, IL-1, IL-6 and other pro-inflammatory cytokines.

Also provided is a system for providing pain relief medication in a mammalian subject, the system comprising a depot for providing controlled and directed delivery of at least one siRNA molecule to a target site in a subject in need thereof comprising an effective amount of a composition comprising at least one siRNA molecule which decreases inflammation at the target site. In another embodiment, the siRNA molecule further comprises a modified release pharmaceutical composition. The system can further comprise two or more siRNA molecules. In still another embodiment, a catheter is provided rather than a depot. In this embodiment, a catheter has a proximal end and a distal end, the distal end having an opening to deliver a pharmaceutical in situ, the proximal end being fluidly connected to a pharmaceutical pump. In another embodiment, the distal end of the catheter delivers the siRNA molecule within about 10 cm of, or closer to, the target site. In another embodiment, the catheter delivers the siRNA molecule within about 5 cm of, or closer to, the target site. In this system, the at least one siRNA molecule may inhibit inflammation mediated by TNF-α. The system may further comprise a therapeutically effective amount of at least one osteoinductive factor. Suitable osteoinductive factors include, but are not limited to, a bone morphogenetic protein, a growth differentiation factor or a biologically active fragment or variant thereof, a LIM mineralization protein or a biologically active fragment or variant thereof, or combinations thereof. In one embodiment, the system of the invention employs a depot comprising a modified release pharmaceutical carrier.

DETAILED DESCRIPTION

For the purposes of promoting an understanding of the principles of the invention, reference will now be made to preferred embodiments and specific language will be used to describe the same. It will nevertheless be understood that no limitation of the scope of the invention is thereby intended, such alterations and further modifications of the invention, and such further applications of the principles of the invention as illustrated herein, being contemplated as would normally occur to one skilled in the art to which the invention relates.

To aid in the understanding of the invention, the following non-limiting definitions are provided:

The term "gene" refers to a DNA sequence that comprises control and coding sequences necessary for the production of a polypeptide or its precursor. The polypeptide can be encoded by a full length coding sequence (either genomic DNA or cDNA) or by any portion of the coding sequence so long as the desired activity is retained. In some aspects, the term "gene" also refers to an mRNA sequence or a portion thereof that directly codes for a polypeptide or its precursor.

The term "transfection" refers to the uptake of foreign DNA by a cell. A cell has been "transfected" when exogenous (i.e., foreign) DNA has been introduced inside the cell membrane. Transfection can be either transient (i.e., the introduced DNA remains extrachromosomal and is diluted out during cell division) or stable (i.e., the introduced DNA integrates into the cell genome or is maintained as a stable episomal element).

"Cotransfection" refers to the simultaneous or sequential transfection of two or more vectors into a given cell.

The term "promoter element" or "promoter" refers to a DNA regulatory region capable of binding an RNA polymerase in a cell (e.g., directly or through other promoter-bound proteins or substances) and initiating transcription of a coding sequence. A promoter sequence is, in general, bounded at its 3' terminus by the transcription initiation site and extends upstream (5' direction) to include the minimum number of bases or elements necessary to initiate transcription at any level. Within the promoter sequence may be found a transcription initiation site (conveniently defined, for example, by mapping with nuclease S1), as well as protein binding domains (consensus sequences) responsible for the binding of RNA polymerase. The promoter may be operably associated with other expression control sequences, including enhancer and repressor sequences.

The term "in operable combination", "in operable order" or "operably linked" refers to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "vector" refers to a nucleic acid assembly capable of transferring gene sequences to target cells (e.g., viral vectors, non-viral vectors, particulate carriers, and liposomes). The term "expression vector" refers to a nucleic acid assembly containing a promoter which is capable of directing the expression of a sequence or gene of interest in a cell. Vectors typically contain nucleic acid sequences encoding selectable markers for selection of cells that have been transfected by the vector. Generally, "vector construct," "expression vector," and "gene transfer vector," refer to any nucleic acid construct capable of directing the expression of a gene of interest and which can transfer gene sequences to target cells. Thus, the term includes cloning and expression vehicles, as well as viral vectors.

The term "antibody" refers to a whole antibody, both polyclonal and monoclonal, or a fragment thereof, for example a F(ab)$_2$, Fab, FV, VH or VK fragment, a single chain antibody, a multimeric monospecific antibody or fragment thereof, or a bi- or multi-specific antibody or fragment thereof. The term also includes humanized and chimeric antibodies.

The term "treating" or "treatment" of a disease refers to executing a protocol, which may include administering one or more drugs to a patient (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols which have only a marginal effect on the patient.

The term "patient" refers to a biological system to which a treatment can be administered. A biological system can include, for example, an individual cell, a set of cells (e.g., a cell culture), an organ, a tissue, or a multi-cellular organism. A patient can refer to a human patient or a non-human patient.

The present invention provides an advantageous strategy for reducing inflammation associated with any medical condition or procedure. By way of example only, disclosed are compounds and methods for reducing inflammatory response associated with grafting procedure.

In all aspects of the invention localized delivery of an anti-inflammatory agent will obviate or at least minimize the majority of negative side effects of systemic agents. Local delivery of siRNA molecules can be used to achieve high concentrations at the intended target site while using a low dose and minimizing risk of systemic side effects. In addition, incorporation of these agents into a biodegradable depot implant will allow for a protracted release of the agent for long term relief. Aspects of the present invention provide incorporation of these siRNA molecules into biodegradable materials that will act as a depot for localized release of the agent.

Aspects of the present invention provide reagents, methods and systems for inhibiting expression of a pro-inflammatory cytokine in a cell using siRNA molecules that correspond to at least a portion of a pro-inflammatory cytokine nucleic acid sequence. Applicants have found that siRNA molecules targeted to pro-inflammatory cytokine mRNA are effective in inhibiting expression of pro-inflammatory cytokine, thereby providing improved methods for treating inflammation in a subject. The methods of the present invention can be performed utilizing routine techniques in the field of molecular biology. Basic texts disclosing general molecular biology methods include Sambrook et al., *Molecular Cloning, A Laboratory Manual* (3d ed. 2001) and Ausubel et al., *Current Protocols in Molecular Biology* (1994). More specialized texts relevant to the present invention include Sohail, *Gene Silencing by RNA Interference: Technology and Application* (2004).

One aspect of the present invention provides a siRNA molecule corresponding to at least a portion of a pro-inflammatory cytokine nucleic acid sequence capable of inhibiting expression of a pro-inflammatory cytokine in a cell. siRNAs are typically short (19-29 nucleotides), double-stranded RNA molecules that cause sequence-specific degradation of complementary target mRNA known as RNA interference (RNAi) (Bass, *Nature* 411:428 (2001)). Accordingly, in some embodiments, the siRNA molecules comprise a double-stranded structure comprising a sense strand and an antisense strand, wherein the antisense strand comprises a nucleotide sequence that is complementary to at least a portion of a pro-inflammatory cytokine nucleic acid sequence and the sense strand comprises a nucleotide sequence that is complementary to at least a portion of the nucleotide sequence of said antisense region, and wherein the sense strand and the antisense strand each comprise about 19-29 nucleotides.

Any pro-inflammatory cytokine nucleic acid sequence can be targeted by the siRNA molecules of the present invention. Nucleic acid sequences encoding a pro-inflammatory cytokine from various species are publicly available from Genbank and include human (NM_002667), mouse (NM_023129), rat (NM_022707), chicken (NM_205410), dog (NM_001003332), pig (NM_214213), and rabbit (Y00761). Preferably, the targeted pro-inflammatory cytokine nucleic acid sequence is mammalian, more preferably human.

The siRNA molecules targeted to a pro-inflammatory cytokine can be designed based on criteria well known in the art (e.g., Elbashir et al., *EMBO J.* 20:6877 (2001)). For example, the target segment of the target mRNA preferably should begin with AA (most preferred), TA, GA, or CA; the GC ratio of the siRNA molecule preferably should be 45-55%; the siRNA molecule preferably should not contain three of the same nucleotides in a row; the siRNA molecule preferably should not contain seven mixed G/Cs in a row; the siRNA molecule preferably should comprise two nucleotide overhangs (preferably TT) at each 3' terminus; the target segment preferably should be in the ORF (open reading frame) region of the target mRNA and preferably should be at least 75 bp after the initiation ATG and at least 75 bp before the stop codon; and the target segment preferably should not contain more than 16-17 contiguous base pairs of homology to other coding sequences.

Based on some or all of these criteria, preferred pro-inflammatory cytokine siRNA target sequences have been identified in human pro-inflammatory cytokine mRNA (Genbank Acc. No. NM_002667), mouse pro-inflammatory cytokine mRNA (Genbank Acc. No. NM_023129) and rat pro-inflammatory cytokine mRNA (Genbank Acc. No. NM_022707) and are set forth in SEQ ID NOs: 1-9, 10-11 and 12-13, respectively. Other siRNA molecules targeted to pro-inflammatory cytokine can be designed by one of skill in the art using the aforementioned criteria or other known criteria (e.g., Gilmore et al., *J. Drug Targeting* 12:315 (2004); Reynolds et al., *Nature Biotechnol.* 22:326 (2004); Ui-Tei et al., *Nucleic Acids Res.* 32:936 (2004)). Such criteria are available in various web-based program formats useful for designing and optimizing siRNA molecules (e.g., siDESIGN Center at Dharmacon; BLOCK-iT RNAi Designer at Invitrogen; siRNA Selector at Wistar Institute; siRNA Selection Program at Whitehead Institute; siRNA Design at Integrated DNA Technologies; siRNA Target Finder at Ambion; and siRNA Target Finder at Genscript).

siRNA molecules targeted to a pro-inflammatory cytokine can be produced in vitro by annealing two complementary single-stranded RNA molecules together (one of which matches at least a portion of a pro-inflammatory cytokine nucleic acid sequence) (e.g., U.S. Pat. No. 6,506,559) or through the use of a short hairpin RNA (shRNA) molecule which folds back on itself to produce the requisite double-stranded portion (Yu et al., *Proc. Natl. Acad. Sci. USA* 99:6047 (2002)). Such single-stranded RNA molecules can be chemically synthesized (e.g., Elbashir et al., *Nature* 411: 494 (2001)) or produced by in vitro transcription using DNA templates (e.g., Yu et al., *Proc. Natl. Acad. Sci. USA* 99:6047 (2002)). When chemically synthesized, chemical modifications can be introduced into the siRNA molecules to improve biological stability. Such modifications include phosphorothioate linkages, fluorine-derivatized nucleotides, deoxynucleotide overhangs, 2'-O-methylation, 2'-O-allylation, and locked nucleic acid (LNA) substitutions (Dorset and Tuschl, *Nat. Rev. Drug Discov.* 3:318 (2004); Gilmore et al., *J. Drug Targeting* 12:315 (2004)).

siRNA molecules targeted to a pro-inflammatory cytokine can be introduced into cells to inhibit pro-inflammatory cytokine expression. Accordingly, another aspect of the present invention provides a method for inhibiting expression of a pro-inflammatory cytokine in a cell comprising introducing into a cell at least one siRNA molecule that corresponds to at least a portion of a pro-inflammatory cytokine nucleic acid sequence. Although any cell can be targeted, the cell into which the siRNA molecules are introduced is preferably a bone cell, more preferably a osteocyte, a cartilage cell, an annulus fibrosus cell or a nucleus pulposus cell. In some embodiments, the bone cell is from a patient suffering from inflammation, preferably a human patient.

The siRNA molecules produced herein can be introduced into cells in vitro or ex vivo using techniques well-known in the art, including electroporation, calcium phosphate co-precipitation, microinjection, lipofection, polyfection, and conjugation to cell penetrating peptides (CPPs). The siRNA molecules can also be introduced into cells in vivo by direct delivery into synovial joints of tissue, or systemic delivery into the blood stream or nasal passage using naked siRNA molecules or siRNA molecules encapsulated in biodegradable polymer microspheres (Gilmore et al., *J. Drug Targeting* 12:315 (2004)).

Alternatively, siRNA molecules targeted to pro-inflammatory cytokine can be introduced into cells in vivo by endogenous production from an expression vector(s) encoding the sense and antisense siRNA sequences. Accordingly, another aspect of the present invention provides an expression vector comprising at least one DNA sequence encoding a siRNA molecule corresponding to at least a portion of a pro-inflammatory cytokine nucleic acid sequence capable of inhibiting expression of pro-inflammatory cytokine in a cell operably linked to a genetic control element capable of directing expression of the siRNA molecule in a cell. Expression vectors can be transfected into cells using any of the methods described above.

Genetic control elements include a transcriptional promoter, and may also include transcription enhancers to elevate the level of mRNA expression, a sequence that encodes a suitable ribosome binding site, and sequences that terminate transcription. Suitable eukaryotic promoters include constitutive RNA polymerase II promoters (e.g., cytomegalovirus (CMV) promoter, the SV40 early promoter region, the promoter contained in the 3' long terminal repeat of Rous sarcoma virus (RSV), the herpes thymidine kinase (TK) promoter, and the chicken beta-actin promoter), tissue-specific RNA polymerase II promoters, and RNA polymerase III promoters (e.g., U6, H1, 7SK and 7SL).

In some embodiments, the sense and antisense strands of siRNA molecules are encoded by different expression vectors (i.e., cotransfected) (e.g., Yu et al., *Proc. Natl. Acad. Sci. USA* 99:6047 (2002). In other embodiments, the sense and antisense strands of siRNA molecules are encoded by the same expression vector. The sense and antisense strands can be expressed separately from a single expression vector, using either convergent or divergent transcription (e.g., Wang et al., *Proc. Natl. Acad. Sci, USA* 100:5103 (2003); Tran et al., *BMC Biotechnol.* 3:21 (2003)). Alternatively, the sense and antisense strands can be expressed together from a single expression vector in the form of a single hairpin RNA molecule, either as a short hairpin RNA (shRNA) molecule (e.g., Arts et al., *Genome Res.* 13:2325 (2003)) or a long hairpin RNA molecule (e.g., Paddison et al., *Proc. Natl. Acad. Sci. USA* 99:1443 (2002)).

Although numerous expression vectors can be used to express siRNA molecules in cells (Dorsett and Tuschl, Nat. *Rev. Drug Discov.* 3:318 (2004)), viral expression vectors are preferred, (e.g., alphaviral, lentiviral, retroviral, adenoviral, adeno-associated viral (AAV)) (Williams and Koch, *Annu. Rev. Physiol.* 66:49 (2004); del Monte and Hajjar, *J. Physiol.* 546.1:49 (2003). Both adenoviral and AAV vectors have been shown to be effective at delivering transgenes (including transgenes directed to pro-inflammatory cytokine) into mammalian cells, (e.g., Iwanaga et al., *J. Clin. Invest.* 113:727 (2004); Seth et al., *Proc. Natl. Acad. Sci. USA* 101:16683 (2004); Champion et al., *Circulation* 108:2790 (2003); Li et al., *Gene Ther.* 10:1807 (2003); Vassalli et al., *Int. J. Cardiol.* 90:229 (2003); del Monte et al., *Circulation* 105:904 (2002); Hoshijima et al., *Nat. Med.* 8:864 (2002); Eizema et al., *Circulation* 101:2193 (2000); Miyamoto et al., *Proc. Natl. Acad. Sci. USA* 97:793 (2000); He et al., *Circulation* 100:974 (1999). Recent reports have demonstrated the use of AAV vectors for sustained gene expression in mouse and hamster cells for over one year (Li et al., *Gene Ther.* 10:1807 (2003); Vassalli et al., *Int. J. Cardiol.* 90:229 (2003)). In particular, expression vectors based on AAV serotype 6 have been shown to efficiently transduce muscle cells (e.g., Blankinship et al., *Mol. Ther.* 10:671 (2004)). The present invention also provides for the use of coxsackie viral vectors for delivery of pro-inflammatory cytokine siRNA.

Following introduction of the pro-inflammatory cytokine siRNA molecules into cells, changes in pro-inflammatory cytokine gene product levels can be measured if desired. Pro-inflammatory cytokine gene products include, for example, pro-inflammatory cytokine mRNA and pro-inflammatory cytokine polypeptide, and both can be measured using methods well-known to those skilled in the art. For example, pro-inflammatory cytokine mRNA can be directly detected and quantified using, e.g., Northern hybridization, in situ hybridization, dot and slot blots, or oligonucleotide arrays, or can be amplified before detection and quantitation using, e.g., polymerase chain reaction (PCR), reverse-transcription-PCR (RT-PCR), PCR-enzyme-linked immunosorbent assay (PCR-ELISA), or ligase chain reaction (LCR).

Pro-inflammatory cytokine polypeptide (or fragments thereof) can be detected and quantified using various well-known immunological assays, such as, e.g., enzyme-linked immunosorbent assay (ELISA), radioimmunoassay (RIA), immunoprecipitation, immunofluorescence, and Western blotting. Anti-pro-inflammatory cytokine antibodies (preferably anti-human pro-inflammatory cytokine) for use in immunological assays are commercially available from, e.g., EMD Biosciences (San Diego, Calif.), Upstate (Charlottesville, Va.), Abcam (Cambridge, Mass.), Affinity Bioreagents (Golden, Colo.) and Novus Biologicals (Littleton, Colo.), or may be produced by methods well-known to those skilled in the art.

The use of siRNA molecules to inhibit cellular expression of pro-inflammatory cytokine finds utilities as methods for the treatment inflammation in subjects. Accordingly, another aspect of the present invention provides a method for treating a patient suffering from inflammation comprising introducing into said patient at least one siRNA molecule that corresponds to at least a portion of a pro-inflammatory cytokine nucleic acid sequence. Such a method for treatment of inflammation can be performed using systems that provide for the delivery of siRNA molecules targeted to pro-inflammatory cytokine to a tissue. Accordingly, another aspect of the present invention provides a system for treating a patient suffering from inflammation comprising at least one siRNA molecule that corresponds to at least a portion of a pro-inflammatory cytokine nucleic acid sequence and a means for introducing the siRNA molecule into the tissue of the patient. In preferred embodiments, the patient is human.

Numerous well-known methods exist for tissue gene delivery, such as for example, catheter, syringe or depot implant. A preferred delivery system includes a depot implant. A depot implant of the present invention comprises a physical structure to facilitate implantation and retention in a desired location of a subject, such as for example, a synovial joint, a disc space, a spinal canal, or a tissue of a subject; and a siRNA molecule that provides a concentration gradient for targeted delivery of the siRNA molecule to the location. The implant of the present invention provides an optimal drug concentration gradient of the siRNA molecule at a distance of about 1 cm to about 5 cm from the implant. The implant of the present invention may further comprise an insertion cannula for delivery of the siRNA molecule to the subject.

Another aspect of the present invention provides a method for delivering a siRNA molecule to a synovial joint, disc space, a spinal canal, or a soft tissue surrounding the spinal canal of a subject, comprising inserting within the synovial joint, the disc space, the spinal canal, or the soft tissue surrounding the spinal canal of a subject a drug depot implant comprising microspheres, the microspheres comprising a siRNA molecule that provides a concentration gradient for targeted delivery of the agent to the subject, wherein the microspheres are injected into the synovial joint, the disc space, the spinal canal, or the soft tissue surrounding the spinal canal.

Another aspect of the present invention provides a method for delivering a siRNA molecule to a synovial joint, a disc space, a spinal canal, or a soft tissue surrounding the spinal canal of a subject, the method comprising inserting within the synovial joint, the disc space, the spinal canal, or the soft tissue surrounding the spinal canal of a subject a drug depot implant comprising a gel in viscous form and microspheres loaded with a siRNA molecule. The combination of gel and microspheres are positioned into the synovial joint, the disc space, the spinal canal, or the soft tissue surrounding the spinal canal of a subject. In one embodiment of the present invention, the gel is a sprayable or injectable adherent gel that hardens upon contact with tissue.

A person of ordinary skill in the art will appreciate that the pro-inflammatory cytokine siRNA target sequences may also be delivered on the carrier and/or in a sustained-release formulation.

Sustained-Release Formulations:

In another embodiment of the present invention, the pro-inflammatory cytokine siRNA target sequences, and, optionally, the additive may be presented in a sustained-release formulation. Suitable sustained-release formulations include but not limited to capsules, microspheres, particles, gels, coating, matrices, wafers, pills or other pharmaceutical delivery compositions. The examples of such sustained-release formulations have been described previously, for example, in U.S. Pat. Nos. 6,953,593, 6,946,146, 6,656,508, 6,541,033, 6,451,346, the contents of which are incorporated herein by reference. Many methods of preparation of a sustained-release formulation are known in the art and are disclosed in *Remington's Pharmaceutical Sciences* (18th ed.; Mack Publishing Company, Eaton, Pa., 1990), incorporated herein by reference.

Generally, the pro-inflammatory cytokine siRNA target sequences can be entrapped in semipermeable matrices of solid hydrophobic polymers. The matrices can be shaped into films or microcapsules. Examples of such matrices include, but are not limited to, polyesters, copolymers of L-glutamic acid and gamma ethyl-L-glutamate (Sidman et al. (1983) *Biopolymers* 22:547-556), polylactides (U.S. Pat. No. 3,773,919 and EP 58,481), polylactate polyglycolate (PLGA) such as polylactide-co-glycolide (see, for example, U.S. Pat. Nos. 4,767,628 and 5,654,008), hydrogels (see, for example, Langer et al. (1981) *J. Biomed. Mater. Res.* 15:167-277; Langer (1982) *Chem. Tech.* 12:98-105), non-degradable ethylene-vinyl acetate (e.g. ethylene vinyl acetate disks and poly (ethylene-co-vinyl acetate)), degradable lactic acid-glycolic acid copolyers such as the Lupron Depot™, poly-D-(−)-3-hydroxybutyric acid (EP 133,988), hyaluronic acid gels (see, for example, U.S. Pat. No. 4,636,524), alginic acid suspensions, polyorthoesters (POE), and the like.

Suitable microcapsules can also include hydroxymethylcellulose or gelatin-microcapsules and polymethyl methacrylate microcapsules prepared by coacervation techniques or by interfacial polymerization. See the PCT publication WO 99/24061 entitled "Method for Producing Sustained-release Formulations," wherein a protein is encapsulated in PLGA microspheres, herein incorporated by reference. In addition, microemulsions or colloidal drug delivery systems such as liposomes and albumin microspheres, may also be used. See *Remington's Pharmaceutical Sciences* (18$^{th}$ ed.; Mack Publishing Company Co., Eaton, Pa., 1990). Other preferred sustained-release compositions employ a bioadhesive to retain pro-inflammatory cytokine siRNA target sequences at the site of administration.

The sustained-release formulation may comprise a biodegradable polymer, which may provide for non-immediate release. Non-limiting examples of biodegradable polymers suitable for the sustained-release formulations include poly (alpha-hydroxy acids), poly(lactide-co-glycolide) (PLGA), polylactide (PLA), polyglycolide (PG), polyethylene glycol (PEG) conjugates of poly(alpha-hydroxy acids), polyorthoesters, polyaspirins, polyphosphagenes, collagen, starch, chitosans, gelatin, alginates, dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, polyorthoesters (POE), or any combinations thereof, as described, for example, in the U.S. Pat. No. 6,991,654 and U.S. Pat. Appl. No. 20050187631, each of which is incorporated herein by reference in its entirety.

A person of ordinary skill will appreciate that different combinations of the sustained-release formulations are also suitable for this invention. For example, the practitioner may formulate the at least one pro-inflammatory cytokine siRNA target sequence as a combination of a gel and microspheres loaded with the at least one pro-inflammatory cytokine siRNA target sequence, wherein the combination of gel and microspheres are placed in the bone defect.

In the practice of the invention, the administration is localized and sustained. For example, depending on the carrier, the sustained-release formulations, and the total amount of the pro-inflammatory cytokine siRNA target sequences, the practitioner can choose a combination, which will release the active material over a desired time period ranging between about one day and about six months.

To prevent unforeseen toxic effects of pro-inflammatory cytokine inhibition, therapy can be titrated by starting with a low dose therapy and assessment of the results, followed by additional deliveries as needed.

The reagents, methods and systems of the present invention are also useful for applications in many organs of the subject.

Specific embodiments according to the methods of the present invention will now be described in the following examples. Although the invention herein has been described with reference to particular embodiments, it is to be understood that these embodiments are merely illustrative of the principles and applications of the present invention. It is therefore to be understood that numerous modifications may be made to the illustrative embodiments and that other

EXAMPLES

Example 1

Target Sequences for Pro-inflammatory cytokine IL-6 siRNA

The following pro-inflammatory cytokine siRNA target sequences were identified based on the open reading frames of human pro-inflammatory cytokine mRNA (Genbank Acc. No. NM_002667). The IL-6 target sequences were previously identified (Kettner-Buhrow and Kracht (November 2005) *Suppression Of Stable Cytokine mRNAs using siRNA Oligonucleotides*).

```
Human Pro-inflammatory cytokine IL-6
Target Sequence 1:
5'-TTTATACCAATAAACGGCATTT-3'        (SEQ ID NO: 1)

Human Pro-inflammatory cytokine IL-6
Target Sequence 2:
5'-CCAGTGCCTCTTTGCTGCTT-3'          (SEQ ID NO: 2)
```

Example 2

Inhibition of Pro-Inflammatory Cytokine IL-6 Expression

An siRNA duplex targeting human pro-inflammatory cytokine IL-6 target sequence 1 (SEQ ID NO: 1) was made commercially by MWG Biotech. (Kettner-Buhrow and Kracht, 2006, *Suppression of Stable Cytokine mRNAs Using siRNA Oligonucleotides*). The following oligonucleotides were used for generating the IL-6 siRNA duplex:

```
                                    (SEQ ID NO: 3)
    Oligo 1:   5'-AAATGCCGTTTATTGGTATAAA-3';
    and (SEQ ID NO: 4)
    Oligo 2:   5'-AAGCAGCAAAGAGGCACTGG-3'
```

Cultured KB cells ($3 \times 10^5$) per six wells were transfected with various concentrations of siRNAs (25-200 nM) or with transfection reagent alone (0 nM) using jetSI™-ENDO following the manufacturer's recommended method. Twenty-four hours later, total RNA was harvested from the transfected cells and the amount of pro-inflammatory cytokine IL-6 mRNA in the cells was determined using RT-PCR for mRNA expression of IL-6 oligos 1 and 2 (SEQ ID NOs: 3 and 4, respectively). Relative amounts of pro-inflammatory cytokine IL-6 mRNA in treated cells versus untransfected cells were determined by comparing the relative intensity of the corresponding ethidium bromide stained bands of RT-PCR products subjected to agarose gel electrophoresis. The results showed that transfection of the KB cells with IL-6 siRNA resulted in reduction of pro-inflammatory cytokine IL-6 mRNA by approximately 50% in cells transfected with 25 nM siRNA, as compared to untransfected control cells. These data clearly indicate that transfection of KB cells with siRNA targeting pro-inflammatory cytokine IL-6 results in reduction in the amount of pro-inflammatory cytokine IL-6 expressed by the KB cells.

Example 3

Inhibition of Pro-Inflammatory Cytokine TNF-α Expression

It was also shown that intraperitoneal injection of anti-TNF siRNA in mice reduced peritoneal TNF-α levels (but not IL-1α levels, indicating specificity). The siRNA molecules were selected to target different sites of TNFα mRNA and injected either as a single-stranded (sense or antisense) or as a double-stranded siRNA (sense and antisense for the same site).

The sense strands of ds-siRNAs sequences were as follows:

```
                                    (SEQ. ID. NO.: 5)
    Site 1:    5'-GUGCCUAUGUCUCAGCCUCUU-3'

(SEQ. ID. NO.: 6)
    Site 2:    5'-GAUCAUCUUCUCAAAAUUCUU-3'

(SEQ. ID. NO.: 7)
    Site 3:    5'-GACAACCAACUAGUGGUGCUU-3'

(SEQ. ID. NO.: 8)
    Site 4:    5'-GGAGAAAGUCAACCUCCUCUU-3'

(SEQ. ID. NO.: 9)
    Site 5:    5'-GGCCUUCCUACCUUCAGACUU-3'
```

The ds-siRNA constructs were more efficient than single-stranded constructs. The treatment comprising administering of a double stranded siRNA targeting site 3 (SEQ. ID. NO. 7) was the most efficient.

Further, ds-siRNA concomitantly protected against injection (18 hours after the siRNA delivery) of a lethal dose of LPS. (Sorensen et al. (2003), J. Mol. Biol. 4:327(4):761-6. Importantly, the development of sepsis in mice following a lethal dose of lipopolysaccharide injection, was significantly inhibited by pre-treatment of the animals with anti-TNF-α siRNAs, where the sense sequences were as follows:

```
                                    (SEQ. ID. NO.: 10)
    5'-GACAACCAACUAGUGGUGCdTdT-3',
    and (SEQ. ID. NO.: 11)
    5'-GUGCCUAUGUCUCAGCCUCdTdT-3'.
```

Collectively, these results demonstrate that synthetic siRNAs can function in vivo as pharmaceutical drugs.

Example 4

Depot Implants

In one specific application, the present invention contemplates depot implants. In the following, the term "rod-shaped" is intended to indicate any shape with a longitudinal axis—i.e., is longer along one direction than in other directions; the cross-sectional shape across the longitudinal axis may be any shape, but is preferably elliptical or circular. The implant comprises a rod-shaped (or bullet-shaped) body, which is made from a biodegradable material. The non-biodegradable body could be a porous hollow chamber filled with the therapeutic agent alone or incorporated into a degradable polymer. It may be desirable to make it non-degradable to be able to retrieve it after it has released it's contents. Or the non-biodegradable body could be a small pump that pushed the contents out pores, port(s), or a cannula. Non-limiting examples of suitable biodegradable materials for the body include polyorthoesters (POE), polylacticglycolic acid (PLGA) polysacharides (Saber technology), polycapralactone, polyfumarate, tyrosine polycarbonate, etc. The body is solid, and a siRNA molecule is dispersed throughout the material that forms the body. The dispersal of the siRNA molecule may be even throughout the body. Alternatively, the concentration of the siRNA molecule may vary as a function of the distance from the longitudinal centerline of the body, or as a function of a distance along the longitudinal centerline. As the biodegradable material of the body degrades within the tissue, the siRNA molecule is released. Suitable sustained release materials may be used for the body to carry the one or more siRNA molecule and control the release of the siRNA molecule(s). For example, microspheres may be used to encapsulate the therapeutic agent; the therapeutic agent-containing microspheres are then dispersed through the body. The implant may have a width from about 1 mm to about 6 mm, and a length from about 5 mm to about 20 mm. Selection of suitable lengths and widths for the device will depend upon the targeted implant site, and is well within the abilities of those having ordinary skill in the art.

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed:

1. A method for inhibiting expression of pro-inflammatory cytokine in a intervertebral disc, articulating joint, synovial joint or soft tissue comprising introducing into said joint or tissue a depot implant comprising: a body; a siRNA molecule corresponding to at least a portion of a pro-inflammatory cytokine nucleic acid sequence capable of inhibiting expression of a pro-inflammatory cytokine in a cell, wherein the siRNA molecule is disposed in the body; and the body is capable of eluting the siRNA molecule, and the siRNA molecule comprises a sense strand and the sense strand comprises SEQ ID NO: 7.

2. The method of claim 1, wherein the siRNA molecule is introduced by expression from an expression vector.

3. The method of claim 2, wherein the expression vector is a viral vector.

4. The method of claim 3, wherein the viral vector is an adenoviral vector.

5. The method of claim 3, wherein the viral vector is an adeno-associated viral vector.

6. The method of claim 3, wherein the viral vector is a coxsackie viral vector.

7. The method of claim 1, wherein the pro-inflammatory cytokine is selected from the group consisting of TNF-α, IL-1, and IL-6.

8. A method for treating a subject suffering from inflammation comprising introducing into said subject a depot implant comprising: a body; a siRNA molecule corresponding to at least a portion of a pro-inflammatory cytokine nucleic acid sequence capable of inhibiting expression of a pro-inflammatory cytokine in a cell, wherein the siRNA molecule is disposed in the body; and the body is capable of eluting the siRNA molecule, and the siRNA molecule comprises a sense strand and the sense strand comprises SEQ ID NO: 7.

9. The method of claim 8, wherein the siRNA molecule is introduced by expression from a viral vector.

10. The method of claim 9, wherein the viral vector is an adenoviral vector.

11. The method of claim 9, wherein the viral vector is an adeno-associated viral vector.

12. The method of claim 9, wherein the viral vector is a coxsackie viral vector.

13. The method of claim 8, wherein the patient is human.

14. The method of claim 8, wherein the siRNA molecule is introduced into a joint.

15. The method of claim 8, wherein the pro-inflammatory cytokine is selected from the group consisting of TNF-α, IL-1, and IL-6.

* * * * *